US010813874B2

(12) United States Patent
Lee et al.

(10) Patent No.: US 10,813,874 B2
(45) Date of Patent: *Oct. 27, 2020

(54) COSMETIC ADHESIVE COMPOSITIONS

(71) Applicant: ELC Management LLC, Melville, NY (US)

(72) Inventors: Wilson Lee, Hauppauge, NY (US); Jennifer Ridini, Syosset, NY (US)

(73) Assignee: ELC Management LLC, Melville, NY (US)

( * ) Notice: Subject to any disclaimer, the term of this patent is extended or adjusted under 35 U.S.C. 154(b) by 135 days.

This patent is subject to a terminal disclaimer.

(21) Appl. No.: 15/906,372

(22) Filed: Feb. 27, 2018

(65) Prior Publication Data

US 2018/0369121 A1 Dec. 27, 2018

Related U.S. Application Data

(63) Continuation-in-part of application No. 15/632,903, filed on Jun. 26, 2017.

(51) Int. Cl.
| | |
|---|---|
| A61K 8/81 | (2006.01) |
| A61K 8/34 | (2006.01) |
| A61K 8/26 | (2006.01) |
| A61K 8/87 | (2006.01) |
| A61K 8/73 | (2006.01) |
| A61K 8/85 | (2006.01) |
| A61K 8/36 | (2006.01) |
| A61Q 19/00 | (2006.01) |

(52) U.S. Cl.
CPC ............ *A61K 8/8152* (2013.01); *A61K 8/26* (2013.01); *A61K 8/34* (2013.01); *A61K 8/342* (2013.01); *A61K 8/345* (2013.01); *A61K 8/347* (2013.01); *A61K 8/361* (2013.01); *A61K 8/73* (2013.01); *A61K 8/8176* (2013.01); *A61K 8/85* (2013.01); *A61K 8/87* (2013.01); *A61Q 19/00* (2013.01); *A61K 2800/30* (2013.01); *A61K 2800/33* (2013.01)

(58) Field of Classification Search
CPC .......... A61K 8/8152; A61K 8/26; A61K 8/34; A61K 8/342; A61K 8/345; A61K 8/347; A61K 8/361; A61K 8/73; A61K 8/8176; A61K 8/85; A61K 8/87; A61K 2800/30; A61K 2800/33; A61Q 19/00
See application file for complete search history.

(56) References Cited

U.S. PATENT DOCUMENTS

| | | | |
|---|---|---|---|
| 5,874,072 | A | 2/1999 | Alwattari et al. |
| 7,323,162 | B2 | 1/2008 | Martin et al. |
| 7,682,621 | B2 | 3/2010 | Lamberty et al. |
| 8,920,787 | B2 | 12/2014 | Li et al. |
| 8,932,570 | B2 | 1/2015 | Mu et al. |
| 9,072,686 | B2 | 7/2015 | Bui et al. |
| 9,078,835 | B2 | 7/2015 | Bui et al. |
| 2005/0053567 | A1 | 3/2005 | Liu |
| 2011/0073126 | A1 | 3/2011 | Mu et al. |
| 2015/0004115 | A1 | 1/2015 | Tan et al. |

FOREIGN PATENT DOCUMENTS

| | | |
|---|---|---|
| FR | 2954155 B1 | 2/2012 |
| FR | 2954152 B1 | 12/2012 |

OTHER PUBLICATIONS

ISR and Written opinion of the ISA in related PCT application US2018/038782.

*Primary Examiner* — Matthew P Coughlin
*Assistant Examiner* — Thurman Wheeler
(74) *Attorney, Agent, or Firm* — Peter Giancana

(57) ABSTRACT

Single phase cosmetic adhesive compositions that are flexible and resistant to water below a selected temperature, 43° C. for example. The adhesive compositions wear well, are smudge and flake resistant, as well as oil resistant, making them very suitable for long wear without adhesive failure. Adhesive compositions according to the invention comprise specific combinations of acrylates/VA copolymer and acrylates copolymer in a cosmetically acceptable base or delivery vehicle. Adhesive compositions according to the invention are hydrophilic and easily removed when scrubbed with water above a certain temperature, but not as easily removed with water below that temperature. The adhesive compositions are easy to manufacture, flexible and comfortable, and suitable for use on skin, lips, hair and nails, particularly to secure strips of false eyelashes and eyebrows, as well as individual lash and brow extensions. Cosmetic adhesives of the present invention may also be used to affix glitter or extensions to skin, hair, lips, or nails, and other cosmetic products to keratinic surfaces.

10 Claims, No Drawings

COSMETIC ADHESIVE COMPOSITIONS

FIELD OF THE INVENTION

The present invention is in the field of cosmetic adhesives, such as may be used to secure strips of false eyelashes and eyebrows, as well as individual lash and brow extensions. Cosmetic adhesives of the present invention may also be used to affix glitter to skin, hair or lips, nail extensions, and other cosmetic products to keratinic surfaces.

BACKGROUND

The use of cosmetic treatments that require an adhesive, such as false eyelashes, false eyebrows, false nails and glitter is well established. Also, the use of adhesives in the theater, such as for securing a wig or rubber mask or for affixing an appliance to the skin, is well known. Those adhesives that are more effective at providing long term adhesion without premature failure usually require a complimentary cleanser to remove the adhesive. Sometimes, even with a cleanser, the task of lifting adhesive off of the skin can be very difficult, requiring a harsh abrasive action and multiple washings.

In use, a cosmetic adhesive, may not be visible if the article being affixed covers up the adhesive. At other times, the adhesive may be visible. For example, when using an adhesive to secure false eyelashes, some of the adhesive will be visible after the application is made. Depending on the desired look, this may or may not be beneficial. Either way, an adhesive that can be formulated to achieve the desired look would be advantageous. For example, to blend in or to stand out, the adhesive may be pigmented.

Also, in some applications, it may be advantageous to for the visible adhesive to have a high shine, but that introduces a host of problems that are associated with developing glossy color cosmetics. For example, in general, high shine cosmetic products tend to have little staying power on the skin. Flaking and smudging are common problems with high shine products, unless measures are taken that would not be necessary for non-glossy products. One such measure has been the use of film forming agents in the color composition. Such materials provide a certain level of gloss and staying power, but that gloss is proportional to the amount of film former used. If too much film former is needed to achieve a level of gloss, then the product will be hard, which makes it subject to cracking, and difficult to remove with water alone. Also, hard films can cause discomfort to the wearer. Another issue is that, in film-forming systems, there tends to be a loss of color intensity, true color and/or shine as the solvent evaporates (that is, the composition does not "wear" well). Also, achieving compatibility between film-formers and shine-boosting components, while avoiding stability issues, such as syneresis, has not been a simple task. These issues, as well as the relatively high cost of film-former ingredients, tend to limit the amount of film forming agents that can be used in cosmetic compositions, and limit the level of gloss and color intensity that can be achieved. These problems are further exacerbated by other consumer product demands that must be addressed. These include: perfect adhesive performance for hours at a time, coupled with easy removal from the skin, flexibility of the product on the skin to avoid cracking, or adhesive failure, and the ability of coloring agents to show through a base to give a true color.

There is, therefore, still a need for high shine, pigmented, cosmetic adhesive compositions that meet these, and other, consumer demands. It will be especially advantageous to provide high gloss cosmetic adhesive compositions that offer long wear without adhesive failure, reduced flaking, reduced smudging and true color, as well as easy removal with warm water. The present invention provides such compositions.

Cosmetic compositions that comprise acrylates polymers have typically been provided in the form of emulsions containing oils, surfactants, and/or emulsifiers or anhydrous formulations containing volatile components such as oils or alcohols. For example, U.S. Pat. No. 7,323,162 discloses silicone in water emulsions that comprises a water phase, an oil phase, and two kinds of film formers (a water-soluble, oil resistant film former, such as Covacryl A15 or E14, and an oil soluble (water resistant) film former, at least one of which is a particular silicone-modified acrylates copolymer. The compositions further include a surfactant which is specifically adapted to stabilize silicone in water emulsions.

In contrast, co-owned U.S. Pat. No. 8,932,570 discloses transfer-resistant, single phase aqueous cosmetic compositions. The compositions consist essentially of 1%-95% of a water-soluble, film-forming acrylates copolymer and 1%-60% of a water-soluble plasticizer for the copolymer, and, optionally, 1%-20% pigment. The acrylates copolymer, consists essentially of a monomer selected from the group consisting of acrylic acid and methacrylic acid and a co-monomer selected from the group consisting of alkyl and alkoxyl acrylates and alkyl and alkoxyl methacrylates. The plasticizer may be selected from polyether derivatives, polyoxypropylene derivatives, glycol and glycol derivatives and glycerin and glycerin derivatives, and combinations thereof. The compositions contain no oils, waxes, surfactants or emulsifiers, are water- and oil-resistant upon drying on the skin, and exhibit high gloss and long-wear and transfer-resistant properties. When these compositions contain pigments, they also demonstrate high color intensity. The compositions are useful as eyeliner, mascara, lip gloss, and lip liner. In contrast with two phase oil and water emulsion systems, these compositions are less complex and less costly to formulate, requiring only a single aqueous phase, and no oils, surfactants, or emulsifiers. Additionally, these compositions may be formulated with a single type of water-soluble film former. Nevertheless, U.S. Pat. No. 8,932,570 fails to disclose a cosmetic adhesive composition comprising 20% to 30% of acrylates/VA copolymer and 0.5% to 2.5% of acrylates copolymer as disclosed herein. Nor does it disclose ratios of these materials as disclosed herein, nor their usefulness. The relevance of a minimum water temperature combined with shear to remove the adhesive compositions from the skin, lips, hair or nails is not disclosed. How to adjust an adhesive composition to have a set minimum water temperature for removal is neither disclosed nor suggested.

SUMMARY

The present invention provides cosmetic adhesive compositions that are flexible and resistant to water below 43° C. The adhesive compositions may be formulated with or without pigments and may or may not display high shine. The adhesive compositions wear well, are smudge and flake resistant, as well as oil resistant, making them very suitable as high shine, long wear cosmetics. Adhesive compositions according to the invention comprise specific combinations of acrylates/VA copolymer and acrylates copolymer in a cosmetically acceptable base or delivery vehicle. The adhesive compositions according to the invention are hydrophilic and easily removed when scrubbed with water above a certain temperature, but not as easily removed with water below that temperature. The compositions are easy to manufacture, flexible and comfortable, and suitable for use on skin, lips, hair and nails.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are presented as percentages by weight of the final composition, unless otherwise specified.

Throughout the present specification, "film former" or the like refers to a polymer leaves a film on the substrate to which it is applied, for example, after a solvent accompanying the film former has evaporated, absorbed into and/or dissipated on the substrate.

"Transfer resistant" means that compositions of the invention are not readily removed by contact with another material, such as clothing or water. Transfer resistance may be evaluated by any method known in the art. For example, a composition may be evaluated based on the amount of product transferred from the skin, lips, hair or nails of a wearer to any other substrate, such as clothing. For example, a composition may be transfer resistant if a majority of the product is left on the wearer's skin or hair. Further, the amount transferred may be compared with that transferred by other compositions, such as commercially available compositions. In preferred embodiments of the present invention, little or no adhesive composition is transferred from the skin, lips, hair or nails to another substrate.

"True color" compositions are those in which the color of the applied composition, after a period of time, remains the same or substantially the same as at the time of application to the skin or hair.

Compositions, including adhesive compositions, that maintain color intensity, true color and degree of shine after the solvent evaporates are said to exhibit "good wear" or "long wear".

A "flexible" composition is one that when applied to the skin or hair for its intended use, does not crack or flake for a defined period of time, such as four hours or eight hours of wear. If a composition is not adequately flexible, then it is "rigid".

"Water resistant" means that a composition deposited on the skin, lips, hair or nails, after it has been allowed to dry or cure, does not dissolve or re-wet or absorb moisture or be otherwise adversely affected by the water.

By "single phase" it is intended that the adhesive composition is in a stable homogeneous form rather than in the form of a heterogeneous water-in-oil or oil-in-water emulsion.

"Comprising" and the like, mean that a list of elements may not be limited to those explicitly recited.

Acrylates/VA Copolymer

A first main ingredient of the invention is acrylates/VA copolymer (INCI name), $C_{15}H_{26}O_4$, also known as ethenyl acetate or 2-ethylhexyl prop-2-enoate (IUPAC names); CAS number 25067-02-1. For detailed information, see PubChem Compound Database; CID=168269.

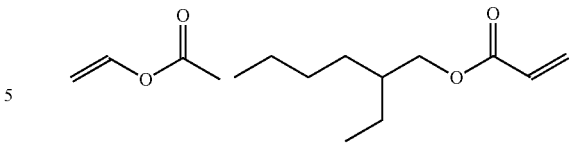

In cosmetics, this material often functions as a binder, film former, adhesive and/or hair fixative. When deployed in aqueous cosmetic systems acrylates/VA copolymer can impart a film on the skin or hair. The pure acrylates/VA copolymer film features a temperature dependence, such that a water rinse of about 40° C. or more will degrade the film, and allow it to be removed from a surface, while retaining its integrity at temperatures at or below normal skin temperature (i.e. 36.5-37.5° C.).

Adhesive compositions of the invention typically comprise 20% to 30% of acrylates/VA copolymer by total weight of the composition, for example 23% to 28%, for example 25% to 26% by total weight of the composition. When levels below about 20% are used, the compositions do not demonstrate good wear, and the degree of shine may suffer. At levels above about 30%, the resulting compositions are too rigid, lacking flexibility.

Acrylates/VA copolymer is commercially available, for example, as Vinysol 2140L from Daido Chemical Corp. Vinysol 2140L is a 46.6% aqueous mixture of acrylates/VA copolymer. Therefore, when using Vinysol 2140L, in order to achieve the concentrations of acrylates/VA copolymer noted above, the concentration of Vinysol 2140L should be about 43% to 64%, for example 50%-60%, for example 55% by total weight of the composition. Vinysol 2140L is reported to have a pH of 4.5, a viscosity of 2,000 mPa-s, a calculated glass transition temperature ($T_g$) of −9° C., while the film exhibits a break elongation of 1,200%, and a break strength of 1.2 MPa (when spread to a thickness 0.1 mm). The strength of the material makes it suitable for thinly applied adhesive cosmetics that will not crack or flake easily. However, at the relatively high concentrations of the present invention, prototype formulations were too rigid to be commercially useful as cosmetic adhesives. The task was to increase the flexibility of the adhesive composition without jeopardizing all of the beneficial properties of the cosmetic system (i.e. tack, break strength, hydrophilicity when wet, hydrophobicity when dry, high gloss, good wear, etc.).

Acrylates Copolymer

To address the problem of high rigidity, the acrylates/VA copolymer was combined with an acrylates polymer that has a lower $T_g$ than acrylates/VA copolymer. In general, a lower $T_g$ provides more flexibility to the resulting film. It also makes the adhesive composition more tacky and have a longer dry time, but in the present invention a longer dry time is a good thing. By itself, acrylates/VA copolymer dries too quickly to be useful as a cosmetic adhesive, where time for application, including positioning, re-positioning and grooming is needed. Of course, an adhesive composition that takes more than a couple of minutes to dry is also not commercially viable. In that amount of time, the article being affixed is likely to move out of place. In the present invention, to provide a suitable dry time, and the right amount of flexibility in the dried adhesive composition, a second main ingredient is acrylates copolymer, $C_{14}H_{22}O_6$, also known as ethyl prop-2-enoate; methyl 2-methylprop-2-enoate or 2-methylprop-2-enoic acid (IUPAC names); CAS number 25133-97-5. For detailed information, see PubChem Compound Database; CID=168299. In various types of cosmetic formulations, acrylates copolymer has a wide variety of uses including as film formers, hair fixatives, binders, and suspending agents, viscosity enhancers, antistatic agents and adhesives. At concentrations discussed herein, the combination of acrylates/VA copolymer and acrylates copolymer has a dry time that is suitable for the cosmetics consumer (which we define as one minute or less), while the increase in tackiness was not so much as to be unreasonable for consumer use. Furthermore, as noted above, acrylates/VA copolymer films feature a temperature dependence, such that a water rinse of at least about 40° C. will degrade the film, but not below this. In combining acrylates/VA copolymer with acrylates copolymer at the ratios disclosed herein, it was noted that the resulting adhesive films exhibit a different minimum temperature of water that is required to degrade the adhesive. Specifically, the addition of acrylates copolymer tends to increase the minimum temperature of water that is required to degrade the adhesive film.

In the present invention, useful concentrations of acrylates copolymer are from 0.5% to 2.5% based on total weight of the composition; for example 1% to 2%, or, for example 1.5%. At concentrations above about 2.5%, the acrylates copolymer becomes disruptive to the performance and stability of the adhesive composition. For example, compositions become too sticky for consumer acceptance. Below about 0.5%, and the acrylates copolymer cannot impart enough flexibility to the final composition, which increases the risk of adhesive failure. Acrylates copolymer is commercially available, for example, as Daitosol 5000AD from Daito Kasei Kogyo Co. Daitosol 5000AD is a 50% aqueous mixture of acrylates copolymer. Therefore, in order to achieve the concentrations of acrylates copolymer noted above, the concentration of Daitosol 5000AD should be about 1% to 5%, for example 2% to 4%, preferably 3% by total weight of the composition. Daitosol 5000AD is reported to have a pH of 5.5-7.5, a viscosity of 50-100 mPa-s, a glass transition temperature ($T_g$) of about −14° C.

Based on the above, we can say that the ratio of the weight of acrylates/VA copolymer to the weight of acrylates copolymer must be in the range 8:1 to 60:1, preferably 12:1 to 40:1, more preferably 16:1 to 20:1.

In the United States, typical water temperatures from a home faucet are set not to exceed 120° F. (48.9° C.). Therefore, the certain minimum temperature should be set between 40° C. and 48.9° C., preferably from 42° C. to 46° C., more preferably from 43° C. to 44° C. In various embodiments of the present invention, the certain minimum temperature is adjusted to be from 43° C. to 44° C. 43° C. to 44° is most preferred because it is several degrees warmer than normal, healthy skin temperature (i.e. 36.5-37.5° C.), but not so high as to damage the skin or cause pain. The minimum temperature of 40° C. reported for the Vinysol 2140L material, is close to normal skin temperature and may not provide a consistent experience in consumer use. By using acrylates/VA copolymer in combination with acrylates copolymer, in the ratios disclosed herein, the minimum temperature could be fixed to be more than 40° C., preferably 42° C. to 46° C. to provide more of a margin of error, or better 43° C. to 44° C.

Form of Adhesive Composition and Other Ingredients

Preferred adhesive compositions of the invention are a single aqueous phase, and have no oil or silicone. Adhesive compositions of the invention may or may not comprise pigments. When the adhesive compositions comprise pigments, the concentration may range from about 0.001% to 30% by weight of the total composition. Greater than about 30% of pigment may introduce an unacceptable level of reduced stability and/or reduced adhesive performance of the composition. Therefore, preferred is from 1% to 20% of pigments, more preferred from 1% to 15% of pigments by weight of the total composition, and still more preferred is 2% to 10% of pigments by weight of the total composition. Compositions of the invention may typically comprise from 40% to 65% of water by weight of the total composition. This amount of water is that from all sources, such as that in Vinysol 2140L and Daitosol 5000AD.

One advantageous feature of the adhesive compositions of the present invention is that they are hydrophilic before and during use, but hydrophobic upon drying. A single phase aqueous cosmetic composition that is hydrophilic prior to application, but that transitions to hydrophobic upon drying is unusual. Examples 1 and 2 are single phase adhesive compositions of the invention, intended to be used in the eye area, and to blend in with black eyelashes or eyebrows, and black mascara. The contact angle of the composition of Example 1 was measured before and after drying. Prior to drying, the adhesive compositions was hydrophilic. Upon drying, the adhesive composition of Example 1 exhibited a contact angle of 42 degrees, which indicates hydrophobicity. This is an unusual dry state for an aqueous, single phase cosmetic adhesive.

| Ingredient | Example 1 % Concentration | Example 2 % Concentration |
|---|---|---|
| [1]Vinysol 2140L | 60.00 | 60.0 |
| [2]Daitosol 5000AD | 3.00 | 1.0 |
| xanthan gum | 0.21 | 0.21 |
| [3]Distinctive ® Ink Black Chip AQ | 3.90 | 6.2 |
| [4]preservative system | 1.22 | 1.1 |
| caustic soda 30% | 0.22 | 0.3 |
| SD alcohol | 3.00 | 3.0 |
| water | Q.S. | Q.S. |

[1]46.6% aqueous mixture of acrylates/VA copolymer.
[2]50% aqueous mixture of acrylates copolymer.
[3]Black 2 (and) Polyester-5 (and) PVP (and) Laureth-4 (40% carbon black).
[4]phenoxyethanol 0.80%, phenylethyl alcohol 0.21%, chloroxylenol 0.21%
[5] phenoxyethanol 0.70%, phenylethyl alcohol 0.20%, chloroxylenol 0.20%

The ability to formulate in an aqueous, hydrophilic state that dries to a hydrophobic state (while having other beneficial properties described herein) is a great advantage of the present invention. While the adhesive composition is in a first or hydrophilic state, the ability to formulate with water soluble ingredients is enhanced, and application of the cosmetic adhesive is easier and feels nicer. When dried to a second or hydrophobic state, the applied adhesive resists breakdown from moisture in the skin and atmosphere.

It may be noted that Vinysol 2140L (acrylates/VA copolymer) has this property of being hydrophilic in a first state and drying to become hydrophobic in a second state. However, it was not a foregone conclusion that the final adhesive compositions would retain this property, nor was it a trivial task to achieve this property in the final adhesive composition. Also, it does not seem that this property has been exploited as we have done. At a minimum, the invention includes adhesive compositions that comprise a significant amount of Vinysol 2140L (at least about 43%) while avoiding ingredients in the composition that would prevent a wet hydrophilic composition from drying to a hydrophobic state, while also delivering long wear, transfer resistance, and, where intended, high shine. Adhesive compositions of the present invention do all of this.

To achieve sufficient hydrophilicity in the first state, the use of hydrophobic materials should be limited to less than about 0.5% based on total weight of the adhesive composition; preferably less than 0.25%. Materials that are partly hydrophilic and partly hydrophobic could possibly exceed these limits, based on the performance of the final composition. In some embodiments of the invention, it is preferable if the adhesive composition comprises no hydrophobic ingredients, such as hydrophobic oils or waxes. Oils are organic substances that are liquid at ambient temperature, such as esters, triglycerides, hydrocarbons and silicones. A typical wax used in cosmetic compositions is carnauba wax. In some embodiments of the invention, it is most preferable if the compositions contain no hydrophobic oils or waxes. Nevertheless, upon drying to a film, the film clearly exhibits hydrophobicity, making it resistant to water. However, unlike anything disclosed in U.S. Pat. No. 8,932,570, the dried compositions of the present invention may be easily washed off with water at or above that certain minimum temperature and an application of shear. Both shear and a certain minimum water temperature are needed to remove the adhesive composition from the skin, lips, hair or nails. For example, when the dried adhesive is exposed to water at or above a certain minimum temperature, the adhesive experiences a breakdown in structure, but does not otherwise dissolve in the applied water, so that the adhesive remains on the keratinic surface. Likewise, when the dried adhesive is exposed to shear (in the form of a typical vigorous scrubbing action), without water or with water below a certain minimum temperature, the adhesive remains in place, having excellent adhesion to the skin, lips, hair or nails. Furthermore, the adhesive maintains its high degree of shine, true color and color intensity, making it especially appropriate as a cosmetic adhesive. To effect the removal of the adhesive composition from the skin, lips, hair or nails, both shear (in the form of a typical vigorous scrubbing action) and water above a certain minimum temperature must be applied to the adhesive in order to lift it off of the keratinic surface. This means that adhesive compositions of the invention can be worn for long periods without adhesive failure. It also means that adhesive compositions of the invention have excellent smudge or transfer resistance.

Various ingredients may be included in the adhesive compositions to fine tune the consumer experience or enhance the performance of the composition. Alcohols, for example, may be useful to speed up drying after application to the skin. Amounts of alcohol up to 5% may be useful. The adhesive compositions may also comprise preservatives as needed, typically up to about 2% by weight of the composition. Also, thickeners, viscosity decreasing agents, and/or pH adjusters may be used as needed to create a consumer acceptable product, typically at levels of less than 1% by weight of the composition. At these levels, the foregoing named ingredients do not seem to adversely affect the cosmetic and commercial properties of the adhesive.

Glycols, also known as diols (chemical compounds comprising two hydroxyl groups) are optional, but sometimes useful in the present invention. Glycols, such as 1,3-propanediol, might typically be used in cosmetics to enhance the freeze-thaw stability of the composition. However, when present glycols may also affect the certain minimum temperature below which the dried composition cannot be easily removed from the skin, lips, hair or nails. Where acrylates copolymer tends to increase the certain minimum temperature, glycols tend to decrease it. Therefore, the use of glycols should be avoided, or at least limited to no more than 4% of total glycols, preferably, less than 1% of total glycols, more preferably less than 0.5% of total glycols. Most preferred is 0% glycols (as in Examples 1 and 2 above), especially when acceptable freeze-thaw stability is achievable without glycols. Furthermore, preferred adhesive compositions of the invention comprise no other ingredient in an amount sufficient to plasticize the acrylates/VA copolymer. This is unlike U.S. Pat. No. 8,932,570 where water-soluble plasticizer, which may be glycol, must be present in the composition in an amount sufficient to plasticize.

Another main concern of the cosmetic composition is that it should avoid optical interference effects in the dried state. That is one reason for providing the adhesive as a single phase aqueous composition, as emulsions tend to be cloudy or milky. Since emulsions are excluded, it is preferable for surfactants and emulsifiers to be avoided, or only present incidentally, in trace amounts. If present in the aqueous adhesive compositions of the invention, any material which demonstrates emulsifier or surfactant properties will have an HLB of less than 12. Therefore, based on total weight of the composition, it is preferable if the adhesive composition comprises no more than 3% of surfactants and/or emulsifiers, more preferably no surfactants or emulsifiers.

Further to avoiding optical interference effects in the dried adhesive film, it is preferable if the adhesive composition comprises no clay particles or undissolved particulate material of any kind at a level that would interfere with the adhesion and/or shine of the dried cosmetic composition. At a minimum, the concentration of clay particles or undissolved particulate material must be limited to a level that does not prevent a desired level of adhesion and/or shine in the dried film. Preferably, adhesive compositions of the invention comprise no more than 0.25% of clay particles or undissolved particulate material, more preferably no clay particles or undissolved particulate material.

Polyurethane tends to make compositions very rigid, and will alter the certain minimum temperature of water required for removal of the film from the skin or hair. Therefore, it is preferred if adhesive compositions of the invention comprise a total of no more than 0.5% of polyurethane. More preferably, adhesive compositions of the invention comprise a total of no more than 0.001% of polyurethane. Most preferably, adhesive compositions of the invention comprise no polyurethane.

Agents that significantly interfere with the structure of the dried adhesive film will alter the certain minimum temperature of water required for removal of the film from the skin, lips, hair or nails, as well degrade the tackiness, shine or color. Therefore, it is preferred if adhesive compositions of the invention comprise a total of no more than 0.5% of structuring agents, such as Carbopol®, wax, clay (such as bentonite) or stearic acid. More preferably, adhesive compositions of the invention comprise a total of no more than 0.001% of structuring agents. Most preferably, adhesive compositions of the invention comprise no structuring agents. A useful exception to this rule is sodium stearate. Unlike many structuring agents, sodium stearate is partly hydrophilic, which makes it suitable for an aqueous system. Although sodium stearate is partly hydrophobic, its use has not appeared to compromise the objectives of the present invention. This makes it especially useful in embodiments of the present invention when a structuring agent may be needed. Sodium stearate may be used as a structuring agent up to 4% by weight of the total adhesive composition, More than that amount will begin to disrupt the acrylic bond strength which translates to less water resistance.

Solids that do not dissolve in the aqueous adhesive compositions of the present invention should also be minimized or avoided altogether, as they alter the certain minimum temperature of water required for removal of the film from the skin, lips, hair or nails, as well degrade the shine.

The following non-limiting examples illustrate additional embodiments of the invention.

Examples 3-5

| Phase | Ingredient | Example 3 | Example 4 | Example 5 |
|---|---|---|---|---|
| | | % Concentration | | |
| 1 | sodium stearate C-7 | | | 4.0 |
| 2 | [1]Vinysol 2140L | 55.0 | 60.0 | 47.4 |
| 2 | [2]Daitosol 5000AD | 2.0 | 3.0 | 2.5 |
| 3 | 1,3-propanediol | 4.0 | 4.0 | 4.0 |
| 4 | [3]Distinctive ® Ink Black Chip AQ | | 3.9 | |
| 4 | pigments | 20.0 | | 12.0 |
| 5 | [4]preservative | 0.8 | 0.9 | 0.4 |
| 6 | xanthan gum | 0.3 | 0.3 | 0.4 |
| 7 | caustic soda 30% | 0.2 | 0.2 | 0.2 |
| 8 | SD alcohol | 3.0 | 3.0 | 3.6 |
| | water | Q.S. | Q.S. | Q.S. |

[1]46.6% aqueous mixture of acrylates/VA copolymer.
[2]50% aqueous mixture of acrylates copolymer.
[3]Black 2 (and) Polyester-5 (and) PVP (and) Laureth-4 (40% carbon black).
[4]phenoxyethanol 80%; chloroxylenol 20%.

The procedure for preparing the adhesive compositions is simple, and as follows.
1. Mix and dissolve the acrylates/VA copolymer and acrylates copolymer in a portion of water (this step may be omitted when working with these materials already supplied solution; i.e Vinysol 2140L and Daitosol 5000AD).
2. Stepwise, add the remaining ingredients, mixing well to achieve a uniform mass.

Sometimes, but not always, the degree of gloss or shine of a cosmetic adhesive according to the present invention may be important from a consumer point of view. The gloss of the adhesive compositions shown in Examples 2 and 4 was measured with a gloss meter (reflectometer). Measurements were taken a two angles of reflection, 20° and 60°, on a white background and on a black background, for a total of four measurements. A percent reflectance of 10%-70% indicates a semi-gloss appearance, while more than 70% indicates a glossy appearance. The four gloss measurements of Example 2 ranged from 42.5 to 77.2. At 60° reflected angle, the readings were 75.14 and 77.2, both indicating a glossy appearance. The four gloss measurements of Example 4 ranged from 41.7 to 82.8. At 60° reflected angle, the readings were 81.3 and 82.8, both indicating a glossy appearance.

Conventional methods of using adhesive compositions of the invention may be employed. For example, to apply a strip of false eyelashes, an adhesive composition of the invention should be applied to the edge of the strip with an appropriate applicator, such as a brush or sponge. Alternatively, the adhesive composition could be dispensed from a squeeze tube, through an ophthalmic tip orifice directly onto the eyelash strip. Thereafter, the strip should be position on the eyelid within less than about one minute, by which time at least some of the adhesive will have dried, and repositioning the false eyelash strip will be impractical. Alternatively, the adhesive could be applied directly to the eyelid, and then the strip should be position on the eyelid within less than about one minute.

As described herein, the combination of acrylates/VA copolymer and acrylates copolymer are used to form cosmetic adhesives that will not fail, crack or flake easily, while not being too stiff for commercial acceptance. The adhesive compositions exhibit long wear while performing very well in terms of smudging, flaking and high gloss. The compositions have very good break strength and flexibility, are hydrophilic when wet, but hydrophobic when dry. Once applied, the adhesive compositions dry in about one minute or less, exhibit long, smudge free wear, and can be removed easily with water above a certain minimum temperature, such as 43° C. for example, and scrubbing, but not so easily with water below that temperature, which reduces unwanted transfer and smudging. Even scrubbing with water just one degree below the certain minimum temperature is ineffective to remove thoroughly dried adhesive from the skin, lips, hair or nails.

Adhesive compositions of the invention are single phase, transfer-resistant, water based products that provide excellent tack, and if desires, vibrant color with a mirror-like shine. Preferred adhesive compositions comprise no more than 0.5% of hydrophobic materials, no more than 4% glycol, no more than 3% of surfactants and emulsifiers, no more than 0.25% of clay particles or undissolved particulate material, no more than 0.5% of polyurethane. More preferred compositions comprise no hydrophobic materials, no glycol, no surfactants or emulsifiers, no clay particles or undissolved particulate material, and no polyurethane. Once applied, the adhesive dries relatively quickly, but provides enough time to complete the intended cosmetic treatment. The adhesive provides all day wear with no significant failure or smudging in normal and intended use, and removes easily with water of a specified minimum temperature and scrubbing.

What is claimed is:

1. A single phase, aqueous cosmetic adhesive composition comprising, by total weight of the composition:
   20% to 30% of acrylates/VA copolymer;
   0.5% to 2.5% of acrylates copolymer;
   wherein the ratio of the acrylates/VA copolymer to the acrylates copolymer is in the range of 16:1 to 20:1;
   40% to 65% of water;
   no more than 0.5% of hydrophobic oils or waxes;
   no more than 4% glycol;
   no more than 3% of surfactants and emulsifiers;
   no more than 0.25% of clay particles or undissolved particulate material; and
   no more than 0.5% of polyurethane.

2. The adhesive composition of claim 1 having no hydrophobic oils or waxes.

3. The adhesive composition of claim 1 having no surfactants or emulsifiers.

4. The adhesive composition of claim 1 having no clay particles or undissolved particulate material.

5. The adhesive composition of claim 1 having no polyurethane.

6. The adhesive composition of claim 1 having less than 0.5% glycol.

7. The adhesive composition of claim 1 having no hydrophobic oils or waxes, no surfactants or emulsifiers, no clay particles or undissolved particulate material, and no polyurethane.

8. The adhesive composition of claim 1 having no glycol.

9. The adhesive composition of claim 1 having no ingredient in an amount sufficient to plasticize all of the acrylates/VA copolymer.

10. The adhesive composition of claim 1 having 0.001% to 30% of pigments, by weight of the total composition.

* * * * *